United States Patent
Kurihara et al.

[11] Patent Number: 5,785,984
[45] Date of Patent: Jul. 28, 1998

[54] TASTE-MODIFYING METHOD AND BITTERNESS-DECREASING METHOD

[75] Inventors: Kenzo Kurihara, 4-7, Okuzawa 7-chome, Setagaya, Tokyo; Mitsuyoshi Kashiwagi, Chiba; Takeshi Yasumasu, Ibaraki; Yuki Mitsui, Ibaraki; Setsujiro Inaoka, Ibaraki; Yoshihisa Katsuragi, Ibaraki, all of Japan

[73] Assignees: Kao Corporation; Kenzo Kurihara, both of Tokyo, Japan

[21] Appl. No.: 728,192

[22] Filed: Oct. 10, 1996

Related U.S. Application Data

[63] Continuation of Ser. No. 307,573, filed as PCT/JP94/00176, Feb. 4, 1994, abandoned.

[30] Foreign Application Priority Data

| Feb. 5, 1993 | [JP] | Japan | 5-019000 |
| Feb. 9, 1993 | [JP] | Japan | 5-021285 |

[51] Int. Cl.⁶ .................... A61K 47/00; A61K 31/685
[52] U.S. Cl. .................................................. 424/439
[58] Field of Search .......................... 424/439, 450; 514/922, 78

[56] References Cited

U.S. PATENT DOCUMENTS

| 4,216,234 | 8/1980 | Rawlings | 426/2 |
| 4,929,508 | 5/1990 | Sharma | 424/439 |

FOREIGN PATENT DOCUMENTS

| 0518608 | 6/1992 | European Pat. Off. . |
| 62-58960 | 3/1987 | Japan . |
| 63-283735 | 11/1988 | Japan . |
| 479843 | 3/1992 | Japan . |
| 4235136 | 8/1992 | Japan . |

OTHER PUBLICATIONS

English Abstract JP 4–327526; "Solid Pharmaceutical . . . Use"; Nishikawa et al., Nov. 17, 1992, Japio Sect. C., Sect. No. 1043, vol. 17, No. 167, p. 102.

Patent Abstracts of Japan, vol. 017, No. 693 (C–1144), 17 Dec. 1993.

*Primary Examiner*—Gollamudi S. Kishmore
*Attorney, Agent, or Firm*—Birch, Stewart, Kolasch & Birch, LLP

[57] ABSTRACT

The present invention relates to a protein-lipid complex which modifies the taste of a food, pharmaceutical or cosmetic, particularly has the effect of decreasing the bitterness thereof; and a method for modifying the taste of a food, pharmaceutical or cosmetic with the complex, particularly a method for decreasing the bitterness thereof with the complex.

17 Claims, 7 Drawing Sheets

TASTE-MODIFYING METHOD AND BITTERNESS-DECREASING METHOD

This application is a continuation of application Ser. No. 08/307,573 filed on Sep. 22, 1994, now abandoned, which is a 371 of PCT/JP94/00176 filed Feb. 4, 1994.

FIELD OF THE INVENTION

The present invention relates to a taste-modifying agent which removes uncomfortableness such as bitterness from a substance which is orally ingested, such as foods and pharmaceuticals, to impart a good flavor to the substance when the agent is used by adding it to the substance, and a method for modifying the taste of food, pharmaceutical or the like with the taste-modifying agent.

Further, the present invention relates to a bitterness-decreasing agent which can decrease the uncomfortableness such as bitterness given in the oral ingestion of a food, a pharmaceutical, a cosmetic or the like having a bitter taste by adding the agent thereto, and a method for decreasing bitterness with the bitterness-decreasing agent.

DESCRIPTION OF THE RELATED ART

In addition to its primary object, i.e., intake of nutriment or absorption of pharmaceuticals, it is also desirable to get satisfaction caused by sweetness or savoriness and to avoid discomfort due to bitterness in the oral ingestion of a food, a pharmaceutical or the like.

Bitter-tasting substances are generally repellent substances and are often substances which a healthy person should not take in his body. A human being has a biophylactic mechanism for sensing and excluding bitterness in his mouth which is the entrance of the body. And a bitter-tasting substance can be sensed even when it is present in an extremely small amount as compared with other-tasting substances such as sweet-, salty- and sour-tasting substances.

However, a bitter-tasting substance is present in nearly all of the now existent natural substances and human beings have learned the safeness thereof by experience. Further, "enjoyment of bitterness" is one of cultures and human beings enjoy the bitterness of various foods, for example, luxury goods such as coffee, tobacco and tea or fermented foods such as beer and cheese. Thus, bitterness is an important factor for imparting plenty and satisfaction to the table, but the existence thereof is causative of rating a food, a pharmaceutical, a cosmetic or the like low in quality or for inflicting mental distress on human beings.

The presence of an unpleasant bitter taste is serious to food industry. For example, the bitterness of amino acids or peptides present in the products of proteolysis and that of a bitter-tasting substance present in fruit juice lowers the qualitative evaluation of foods. The method of removing a bitter-tasting substance from a food includes a method using an adsorbent, a method using a clathrate compound and a method of adding a sweetening agent. However, these methods described above have many problems that bitterness cannot completely be depressed, that the quality of taste of food is changed, and so forth.

Further, bitterness is significantly problematic also in the medicinal industry. More precisely, nearly all of the pharmaceuticals used as medicines has a bitter taste and decreasing of the bitter taste has become a pharmaceutically significant issue. In particular, the decreasing of the bitter taste is important in preparations for babies and little children. It is difficult for a baby or a little child to take a solid or powdery preparation orally, so that a liquid preparation such as syrup is generally prepared therefor. However, it is very difficult to decrease the bitterness of a liquid preparation. It has been a practice in the prior art to add a sweetening agent and a flavor or an organic acid such as citric acid to decrease the bitterness of a liquid preparation. Further, the development of a pharmaceutical preparation having an easy-to-take dosage form has been desired for the aged, so that studies have been made particularly on the miniaturization of solid preparations, dosage forms which permit oral intake without using water and liquid preparations. Simultaneously therewith, studies have been made also for the purpose of decreasing bitterness.

Under these circumstances, methods such as microcapsulation, use of a coating agent soluble in the stomach, addition of a clathrate compound and chemical modification of chemicals have been proposed as a method for decreasing the bitterness of pharmaceuticals, in addition to the above methods for decreasing the bitterness of liquid preparations. However, there is a problem that bitterness cannot completely be depressed or that the pharmaceuticals to which the methods can be applied are limited in all methods employed. Thus, no effective method of decreasing the bitterness of pharmaceuticals has been found as yet.

Cosmetics for the face and the oral cavity as well as foods and pharmaceuticals have a bitter taste. In particular, it is desirable that skin lotions used for the face, mouthwashs for the oral cavity, dentrifrices and the like be free from any bitter taste. However, some of the surfactants and flavors used as components therein have a bitter taste, so that the kind and amount of usable compounds are often limited.

Although it has been a practice to lessen the bitter taste of such a cosmetic by the addition of a sweetening agent or a specific flavoring material like in the above case of decreasing the bitterness of foods and pharmaceuticals, the effect attained by such means is insufficient for cosmetics containing a strongly bitter component. With respect to cosmetics for the face and oral cavity, particularly, the components which are added for decreasing the bitter taste are problematic in safeness in some cases when the components are orally ingested. Thus, no cosmetic having a sufficiently decreased bitterness has been proposed as yet.

Substances modifying the taste-receptive tissue have been reported as a seasoning agent or a masking agent. For example, it has been known that gymnetic acid contained in the leaf of some asclepiadaceous plants and zizyphine contained in the leaf of a jujube, both of which are triterpene glycosides, have a depression effect upon bitterness. Further, it has been found that miraculin obtained from a miracle fruit which is a fruit of a sapotaceous plant and curculin contained in a hypoxidaceous plant exhibit the effect of making a person taste sweet when the person holds it in his or her mouth and thereafter drinks a sour or tastless water ("Kagaku to Seibutsu (Chemistry and Biology), Vol. 27, No. 6, p.p. 350–352, published on Jun. 25, 1989, edited by the Agricultural Chemical Society of Japan). However, they are problematic in quantity to be supplied, separation and purification, chemical stability, cost and so forth, being difficult to utilize industrially.

Accordingly, an object of the present invention is to provide, at a low cost, a substance (a taste-modifying agent or a bitterness-decreasing agent) which modifies the taste of foods, pharmaceuticals used as medicines and cosmetics, particularly one which decreases the bitterness thereof and which is safe even when ingested orally.

Further, the present invention provides a method for modifying the taste of foods, pharmaceuticals and cosmetics with the above taste-modifying agent easily, particularly, a method for decreasing the bitterness of foods, pharmaceuticals and cosmetics therewith easily.

Further, the inhibitor for bitter taste which has been studied by Katsuragi and Kurihara has been reported in Nature (Vol. 365, p.p. 213–214, published on Sep. 16, 1993) and in the Asahi News Paper (dated Jul. 7, 1993).

DISCLOSURE OF THE INVENTION

The present inventors have directed their attention to the taste reception mechanism occurring in the gustatory organ present on the tongue in the oral cavity and the interaction between a substance having a taste and the taste-receiving membrane and have made extensive studies on modification of taste and decreasing of bitterness. As the result, they have found that the protein-lipid complex according to the present invention adheres to the neighborhood of the bitterness-receptive site in the taste-receiving membrane present on the taste cell of the tongue to exhibit the inhibitory function of the reception of a bitter taste, and that simultaneously with this phenomenon or independently thereof, the complex adsorbs a bitter-tasting substance which is a hydrophobic molecule to lower the concentration of this substance in the system (in the mouth). The present invention has been accomplished on the basis of these findings.

Thus, the present invention provides a protein-lipid complex which is an aggregate of a protein with a lipid and which is useful as a taste-modifying agent, a bitterness-masking agent and a bitterness-decreasing agent.

The protein-lipid complex of the present invention can easily be mass-produced, can be provided at a low cost, is safe even when orally ingested, and exhibits both the function of decreasing bitterness and the function of increasing sweetness and umami.

Further, the present invention provides a method for decreasing bitterness which is characterized by holding the above protein-lipid complex in the oral cavity before and/or simultaneously with the oral ingestion of a bitter-tasting food, pharmaceutical or cosmetic to thereby mask the bitterness-receptive sites present in the oral cavity, a method for decreasing a bitterness of a food, pharmaceutical or cosmetic which comprises adding the above protein-lipid complex to a bitter-tasting food, pharmaceutical or cosmetic, and a method for modifying a taste of a food, pharmaceutical or cosmetic which comprises adding the above protein-lipid complex to a food, pharmaceutical or cosmetic.

Furthermore, the present invention provides an use of the above protein-lipid complex in decreasing a bitterness of a bitter-tasting food, pharmaceutical or cosmetic, and an use of the above protein-lipid complex in modifying a taste of a food, pharmaceutical or cosmetic.

The present invention provides a process for the preparation of a food composition, a medicinal composition or a cosmetic having a decreased bitterness which comprises adding the above protein-lipid complex to a bitter-tasting food, pharmaceutical or cosmetic, and a process for the preparation of a food composition, a medicinal composition or a cosmetic having a modified taste which comprises adding the above protein-lipid complex to a food, pharmaceutical or cosmetic.

The present invention provides a food composition comprising a food and the above protein-lipid complex, a cosmetic comprising a cosmetic component and the above protein-lipid complex, and a medicinal composition comprising a pharmaceutical and the above protein-lipid complex.

The present invention will be described in detail, hereinafter.

The reception of tastes on the tongue is effected through their mechanisms respectively corresponding to substances each having a taste. More precisely, it is presumed that sweetness and amino-acidic tastes are received through their respective receptor proteins, and ion channels participate in the reception of salty and sour tates. While it is known that bitterness is received by the lipid layer of the taste-receiving membrane.

Generally, a bitter-tasting substance has a hydrophobic group to exhibit a high affinity for a lipid membrane. This property has been ascertained by the use of an artificial lipid membrane. That is, when a bitter-tasting substance is added to a lipid membrane containing a fluorescent dyestuff, the fluorescent dyestuff is released. More fluoresent dyestuff is released by the addition of a bitter-tasting substance having a stronger bitter taste. When other-tasting substance is added, no fluoresent dyestuff is released. Accordingly, it is believed that the fluorescent dyestuff is released in place of the bitter-tasting substance adsorbed by the lipid membrane. Thus, the bitter-tasting substance has the property of being easily adsorbable by a lipid membrane. Accordingly, it is reasonable to utilize a lipid membrane in order to decrease bitterness.

However, the handling of a lipid is practically difficult. For example, when a neutral lipid such as a triglyceride, a phospholipid or the like is used to decrease bitterness, an emulsification and dispersion step is necessary for preparing a food, a pharmaceutical or the like having a decreased bitter taste, which is not always practical.

On the contrary, the protein-lipid complex of the present invention can take the form of powder, fine particle or paste, so that it can be mixed to use as such with a food, a pharmaceutical, a cosmetic or the like having a bitter taste, being unproblematic in practical. Further, since a protein is bonded to a lipid in the protein-lipid complex of the present invention, the lipid is improved in its dispersibility in water. Accordingly, when the food, pharmaceutical, cosmetic or the like having a bitter taste is liquid, the complex can also be suspended therein.

As described above, when the protein-lipid complex of the present invention is added to a food, pharmaceutical or cosmetic containing a bitter-tasting component, the bitterness is decreased by the following two effects:

1) when the protein-lipid complex of the present invention is held in the mouth, the complex is adsorbed in the neighborhood of the bitterness-receptive site of the taste cell to hinder the reception of a bitter taste, and
2) a bitter-tasting component is adsorbed by the lipid moiety of the protein-lipid complex of the present invention to lower the concentration of the bitter-tasting substance in the system (in the mouth).

Further, by virtue of the decrease in bitterness attained by the above mechanisms, sweetness and umami can be sensed at an enhanced intensity by the taste receptor, which is presumably a reason why the taste of food or the like can be modified by the use of the protein-lipid complex according to the present invention.

The protein-lipid complex according to the present invention will be described in detail, hereinafter.

The protein to be used in preparing the protein-lipid complex according to the present invention includes animal proteins and/or plant proteins. Specific examples thereof include milk protein, soybean protein, egg protein and wheat protein. In the present invention, it is preferable to use a water-soluble protein, particularly one member selected from among β-lactoglobulin, α-lactoalbumin, casein, serum albumin, ovalbumin, glycinin, actin and myosin, or a mixture of two or more members selected from among them. It is most desirable to use a protein (mixture) comprising at least 30% by weight of β-lactoglobulin.

The lipid to be used in preparing the protein-lipid complex according to the present invention includes monoglycerides, diglycerides, triglycerides, phospholipids, lysophospholipids, glycolipids, sterol lipids, fatty acid esters of polyols, and fatty acids. Among them, phospholipids and lysophospholipids are preferable, and phospholipids are particularly preferable. Further, specific examples of phospholipids include phosphatidylcholine, phosphatidylethanolamine, phosphatidylinositol, phosphatidic acid, phosphatidylserine, phosphatidylglycerol, cardiolipin and sphingomyelin, while those of lysophospholipids include lysophosphatidylcholine and lysophosphatidic acid. Furthermore, as the above phospholipid and lysophospholipid, processed lecithins prepared by subjecting lecithin and/or lecithin analogues originating in animals and/or plants to enzymatic treatment and/or enzymolysis can be used. In addition, as the above phospholipid and lysophospholipid, not only those extracted from natural matters, but also those prepared by chemical or enzymatic synthesis can be used. Specific examples of such phospholipid and lysophospholipid include reaction products prepared by a synthesis method such as esterification of a diglyceride with phosphoric acid, that of a monoglyceride with phosphoric acid and that of glycerophosphoric acid with a fatty acid. Such reaction products include monoacyl glyceromonophosphates, monoacyl glycerodiphosphates, diacyl glyceromonophosphates, bisphosphatidic acid and so forth. Further, examples of the synthetic phospholipid and lysophospholipid include hydrogenated phospholipids and hydrogenated lysophospholipids. Among these lipids, negatively charged acidic phospholipid is particularly preferable. More specifically, preferable examples thereof include phosphatidylinositol, phosphatidic acid, phosphatidylserine, phosphatidylglycerol and cardiolipin.

The protein-lipid complex of the present invention can be prepared as a powdery, fine-particular (granular) or pasty composition by homogeneously dispersing a protein, a lipid and, if necessary, other components in water by mechanical means and/or sonication and then effecting dehydration.

When the protein-lipid complex of the present invention is used for the purpose of decreasing the bitterness of a pharmaceutical, the ratio between the protein incorporated and the lipid incorporated in the preparation of the protein-lipid complex is preferably one that the lipid is from 0.01 to 100 parts (weight ratio) based on 1 part of the protein, and is still more preferably one that the lipid is from 1 to 10 parts (weight ratio) based on 1 part of the protein.

The protein-lipid complex of the present invention is prepared by using water in an amount of preferably from 0.01 to 100 parts (weight ratio), still more preferably from 1 to 10 parts (weight ratio), based on 1 part of the total amount of the protein and the lipid which have been blended at the ratio described above, mixing them, dispersing and emulsifying by mechanical means and/or sonication, and dehydrating the obtained emulsion composition.

When the protein-lipid complex of the present invention is used for the modification of the taste of a food, a cosmetic or the like (including the decreasing of the bitterness thereof), the ratio between the protein incorporated and the lipid incorporated in the preparation of the protein-lipid complex is preferably one that the lipid is from 0.05 to 50 parts (weight ratio) based on 1 part of the protein, and is still more preferably one that the lipid is from 0.4 to 3 parts (weight ratio) based on 1 part of the protein.

In the preparation of an emulsion by mixing a protein with a lipid at the ratio described above and dispersing the obtained mixture in water or by adding a protein and a lipid to water separately and dispersing them, it is preferable to use water in an amount of from 0.5 to 100 parts (weight ratio), still more preferably from 1 to 10 parts (weight ratio) based on 1 part of the total amount of the protein and the lipid.

The emulsification step for preparing the protein-lipid complex according to the present invention can be conducted by the method which comprises premixing a protein with a lipid and dispersing and emulsifying the obtained mixture in a predetermined amount of water, the method which comprises preparing a homogeneous aqueous solution of a protein and dispersing and emulsifying a lipid in the solution or other methods. Any of these methods may be employed. In the dispersion and emulsification, a homogenizer or an emulsifier, an ultrasonic apparatus and the like can be used.

With respect to the emulsifying condition of the emulsion composition, oil-in-water type (O/W type), water-in-oil type (W/O type), multiphase emulsion types such as oil-in-water-in-oil type (O/W/O type), and so forth may be cited. The emulsifying condition is not particularly limited in practice. It is preferable that the particle size of the dispersed phase of the emulsion composition be 0.1 to 100 μm, particularly preferably 0.5 to 10 μm.

Although the temperature at which the blending of a protein with a lipid or the dispersion of a protein and a lipid in water is conduted is not limited, the employment of high temperature causes the degradation of the lipid or the like and the generation of a bad smell in some cases. Accordingly, it is preferable that the temperature be 60° C. or below to prevent such adverse effects. The method of the dehydration is not particularly limited, and known methods can be employed. Examples of the method of the dehydration include means such as vacuum drying, spray drying and freeze drying. It is desirable in the present invention to employ a method which permits rapid dehydration without causing the degradation of the lipid and protein and the contamination with microorganisms.

The form of the protein-lipid complex depends upon the water content and the lipid content. The complex generally contains water in an amount of 20% by weight or below, preferably 12% by weight or below, still more preferably 10% by weight or below.

Next, the method for modifying a taste of a food, pharmaceutical or cosmetic with the use of the above protein-lipid complex and the method for decreasing a bitterness of a food, pharmaceutical or cosmetic therewith will be described in detail.

When the pharmaceutical or the like having a bitter-tasting component is in the form of a liquid or an aqueous solution, the above protein-lipid complex is added to the liquid (or the aqueous solution) in a final concentration of 0.01 to 99% (weight ratio), preferably 0.1 to 20% (weight ratio) and thereafter the obtained mixture is sufficiently agitated to disperse the complex in the liquid. In the stirring and dispersion, a homogenizer, an emulsifier and an ultrasonic apparatus may be used. Further, the obtained stirred dispersion may be converted into a solid such as powder by subjecting it to dehydration.

When the pharmaceutical or the like having a bitter tasting component is in the form of a paste or a solid, the protein-lipid complex is added to the paste or the solid in an amount of at least 0.1 part (weight ratio), preferably 10 to 500 parts (weight ratio) based on 1 part of the paste or the solid, and the obtained mixture is homogenized.

When the protein-lipid complex of the present invention is used for modifying the taste of food or the like, it is preferable to use the complex in an amount of 0.05 to 10% by weight, still more preferably 0.1 to 3.0% by weight based on the total amount (1, i.e., 100% by weight) of the food or the like containing the complex.

When the above protein-lipid complex is used for decreasing the bitterness of a cosmetic, it is preferable to incorporate the complex in a concentration in the cosmetic of 0.05 to 10% by weight, particularly 0.1 to 5% by weight. Further, it is preferable to use the complex in an amount of 1 to 1000 times, particularly 5 to 200 times the weight of the bitter-tasting cosmetic component.

When the complex of the present invention is used for the purpose of decreasing the bitterness of a food, pharmaceutical or cosmetic containing a bitter-tasting component which is difficulty soluble in water, an organic solvent, e.g., an alcohol such as ethanol or a hydrocarbon such as hexane is used, the food or the like is dissolved therein, and then the protein-lipid complex is added thereto.

Foods, to which the taste-modifying agent, taste-modifying method, bitterness-decreasing agent and bitterness-decreasing method according to the present invention can be applied, include grapefruit, orange, lemon and the like and juices thereof; tomato, green pepper, celery, gourd, carrot, potato, asparagus and the like and juices thereof; seasonings such as sauce, soy and miso; soybean foods such as tofu and soybean milk; emulsion foods such as cream, dressing, mayonnaise and margarine; processed marine products such as fish meat, ground fish and fish egg; legumes such as peanut; luxury goods such as beer, coffee, green tea, fermented teas, e.g., black tea, and cocoa; bread; pickles; chewing gum; confectionery for snack; cheese; peppermint; soft drinks; soups such as powdered soup; dairy goods; powdered dairy drinks and noodles.

Further, the complex of the present invention can be used for decreasing the bitternesses of bitter-tasting amino acids such as leucine, isoleucine and phenylalanine, peptides and oligosaccharides which are originating from food.

Furthermore, the complex of the present invention can also be used for decreasing the bitternesses of potassium chloride, magnesium chloride and the like which are used as substitutes for common salt.

Most foods contain a bitter-tasting substance. However, they are generally eaten without sensing the bitterness by virtue of the influence of other tasting components. The protein-lipid complex of the present invention can decrease the disagreeable tastes such as bitter-tasting components in foods to thereby modify the taste thereof.

Pharmaceuticals, to which the taste-modifying agent, taste-modifying method, bitterness-decreasing agent and bitterness-decreasing method according to the present invention can be applied, include bitter-tasting drugs used as medicines. In particular, the complex of the present invention is preferable used for decreasing the bitterness of an acid-addition salt of a basic pharmaceutical. Specific examples thereof include mineral acid salts, such as hydrochloride, nitrate and sulfate, of basic pharmaceuticals; and, further, organic acid salts, such as acetate, citrate, tartrate, maleate, lactate, carbonate, hydrogen-carbonate and borate, of basic pharmaceuticals.

The forms of the bitter-tasting pharmaceuticals themselves or the preparations containing the pharmaceuticals include hydrolyzate (aqueous solution), suspension, emulsion and solid.

If necessary, additives may further be added to the pharmaceutical preparation, i.e., a medicinal composition, which contains the bitterness-decreasing agent according to the present invention. Specific examples of such additives include a filler, a binder, a disintegrator, a lubricant, a fluidizing agent, a coating agent, a corrigent, a masking agent, a flavor and an antioxidant, and one member or two or more members among them may be used.

The granulator used in the preparation step of the pharmaceutical preparation includes planetary mixer, agitation granulator, high-speed mixing granulator, extruding granulator, fluidized-bed granulator, centrifugal tumbling granulator, roller compactor and so forth.

The final dosage form of such pharmaceutical preparation includes a capsule, a granule, a pill, a suspension, an emulsion, a powder, a tablet, an infusion, decoction, troche and so forth. Further, the final dosage form also includes liquid forms such as a liquid preparation, an extract, an elixir, a spirit, a syrup, an aromatic water, a lemonade and a liquid extract.

Cosmetics, to which the taste-modifying agent, taste-modifying method, bitterness-decreasing agent and bitterness-decreasing method according to the present invention can be applied, include those used for the face and those used for the oral cavity. Specific examples of the cosmetics for the face include a skin lotion, a milky lotion, a cream, a face pack, a lip stick, a foundation, a shaving preparation, an after-shave lotion, a cleansing foam and a cleansing gel. The cosmetics for the oral cavity include a dentifrice, a mouthwash, a mouthrinse and so forth.

The bitter-tasting components used as the raw material of these cosmetics include surfactants such as sodium alkyl sulfate and sodium monoalkyl phosphate; fragrances such as menthol, linalool, phenylethyl alcohol, ethyl propionate, geraniol, linalyl acetate and benzyl acetate; antimicrobials such as methyl paraben, propyl paraben and butyl paraben; humectants such as lactic acid and sodium lactate; alcohol-denaturating agents such as sucrose octaacetate and brucine; and astringents such as aluminum lactate.

These cosmetic components are generally contained in a cosmetic in an amount of 0.00001 to 5% by weight.

As described above, the protein-lipid complex of the present invention can be used in a state mixed with a food, pharmaceutical or cosmetic, in other words, as a component of a food composition, medicinal composition or cosmetic composition. Alternatively, the complex may also be used in a manner which comprises holding the protein-lipid complex in the mouth or holding the complex in the mouth and then chewing it, and thereafter holding a food, pharmaceutical or cosmetic containing a bitter-tasting component in the mouth. In this case, the bitterness-decreasing mechanism is one wherein the protein-lipid complex masks the bitterness-receptive sites present in the oral cavity. The protein-lipid complex to be held in the oral cavity in this case may be any of a solid and an aqueous dispersion.

More specifically, the protein-lipid complex is formulated into a powder form such as granule and fine granule; this preparation is added to water or the like in a predetermined amount to suspend or dissolve; and then the suspension or solution thus obtained is held in the oral cavity to thereby mask the bitterness-respective sites. The subsequent oral ingestion of a bitter-tasting pharmaceutical is not accompanied with bitterness. The dosage form of the complex to be used by suspending or dissolving it in water or the like includes those such as a tablet, a effervescent powder and a capsule, in addition to a granule and a fine granule. Alternatively, a liquid preparation such as a syrup and an emulsion, a spray or the like, which is prepared by suspending or dissolving the protein-lipid complex in water or the like, is prepared, and the liquid preparation or the like is held in the oral cavity prior to the oral ingestion of a bitter-tasting food, pharmaceutical or cosmetic.

Furthermore, the bitterness-receptive sites can be masked also by preparing a pharmaceutical, food or drink, which contains the protein-lipid complex of the present invention, such as troche, sweet and chewing gum and holding the pharmaceutical, food or drink in the oral cavity before and/or simultaneously with the oral ingestion of a bitter-tasting food, pharmaceutical or cosmetic.

EXAMPLES

Figure 1:
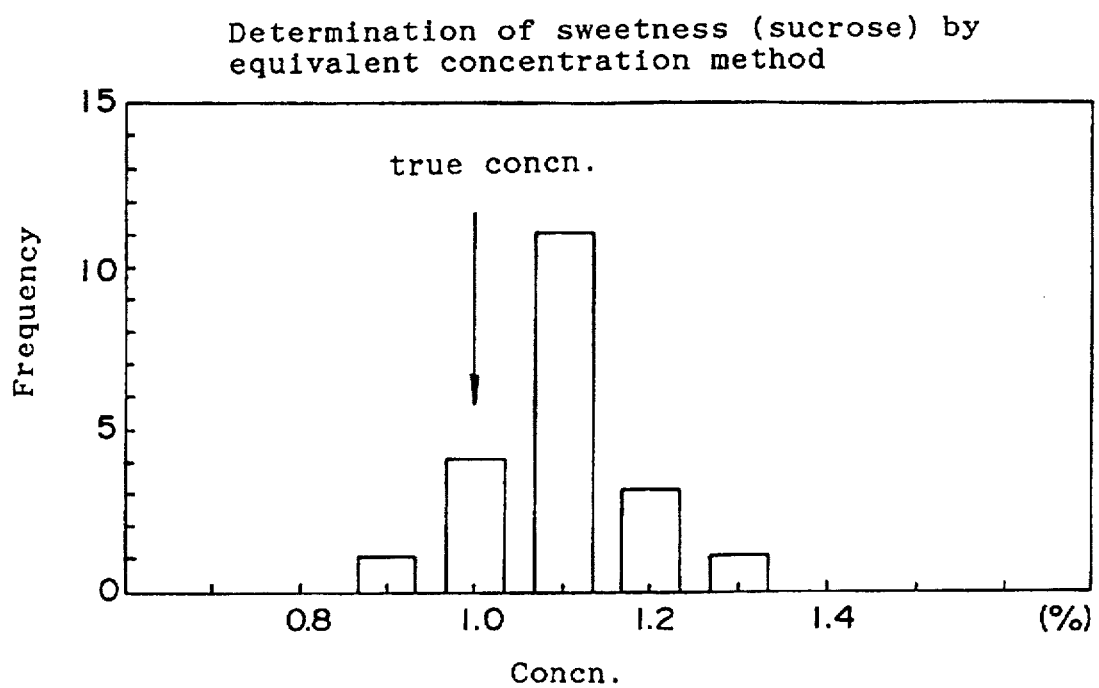
FIG. 1 is a bar graph showing the sweetness-increasing effect of one protein-lipid complex of the present invention.

Although The present invention will be described hereinafter by referring to Examples in more detail, it should not be considered that the Examples limit the scope of the present invention.

Preparative Example 1

100 g of a powdery concentrate of whey protein (trade name: SANRAKUTO N-2, a product of Taiyo Kagaku Co., Ltd.) was kneaded with 40 g of soybean lecithin (trade name: Nissin DX, a product of The Nissin Oil Mills, Ltd.) and the obtained kneaded mixture was dispersed in 1 l of water. Then, the obtained dispersion was agitated by the use of a TK homomixer mfd. by Tokushu Kika Kogyo Co., Ltd. at 9000 rpm for 15 minutes to conduct homogenization. The obtained emulsion was vacuum-dehydrated at 40° C. at 0.1 Torr to reduce the water content of the solid to 9.8%. The obtained massive composition was pulverized and passed through a 20-mesh sieve to give 136 g of a protein-lipid complex powder (Invention sample a).

Preparative Example 2

To the step of the preparation of the emulsion was effected in the same manner as that of the above Preparative Example 1. Then, such emulsion was dried by the use of a freeze dryer to reduce the water content of the solid to 7.8%. The obtained composition was passed through a 20-mesh sieve to give a protein-lipid complex powder (Invention sample b).

Preparative Example 3

100 g of a powdery concentrate of whey protein (trade name: SANRAKUTO N-5, a product of Taiyo Kagaku Co., Ltd.) was dissolved in 1 l of distilled water. 20 g of soybean lecithin (a product of Ajinomoto Co., Ltd.) was added to the obtained aqueous solution in portions under agitating the aqueous solution with a TK homomixer mfd. by Tokushu Kika Kogyo Co., Ltd. at 9000 rpm to emulsify the soybean lecithin at room temperature. The obtained dispersion was freeze-dried to reduce the water content of the solid to 6.5%, giving 108 g of a solid product. This solid product was pulverized with a metal spatula to give a protein-lipid complex powder (Invention sample c).

Preparative Example 4

80 g of soybean lecithin (trade name: Epikuron 200, a product of Lucas Meyer) was dispersed in 1 l of distilled water by sonication. 100 g of a powdery concentrate of milk whey (trade name: Milpro H, a product of San-Ei Kagaku) was added to the obtained dispersion, followed by agitation. The obtained emulsion was freeze-dried to reduce the water content of the solid to 6.8%. The resulting solid product was passed through a 20-mesh sieve to give 167 g of a protein-lipid complex powder (Invention sample d).

Preparative Example 5

80 g of soybean lecithin (trade name: Epikuron 200, a product of Lucas Meyer) was dispersed in 1 l of distilled water by sonication. 40 g of a powdery concentrate of milky whey (trade name: Milpro H, a product of San-Ei Kagaku) and 60 g of sodium caseinate (a product of San-Ei Kagaku) were added to the obtained dispersion, followed by agitation. The obtained emulsion was freeze-dried until the water content of the solid was reduced to 6.8%. The resulting solid product was passed through a 20-mesh sieve to give 170 g of a protein-lipid complex powder (Invention sample e).

Preparative Example 6

80 g of soybean lecithin (trade name: Epikuron 200, a product of Lucas Meyer) was dispersed in 1 l of distilled water by sonication. 100 g of a skimmilk powder (a product of Snow Brani Milk Products Co., Ltd.) was added to the obtained dispersion, followed by agitation. The obtained emulsion was freeze-dried to reduce the water content of the solid to 6.5%. The resulting solid product was passed through a 20-mesh sieve to give 165 g of a protein-lipid complex powder (Invention sample f).

Example 1

Figure 2:
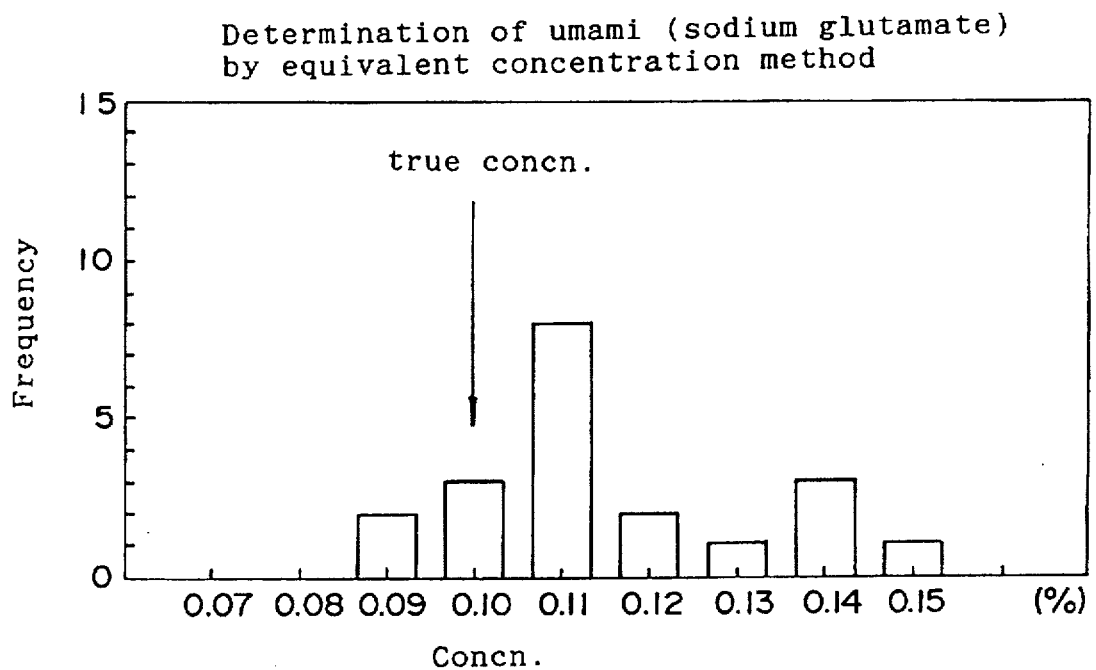
FIG. 2 is a bar graph showing the umami-increasing effect of one protein-lipid complex of the present invention.
Figure 3:
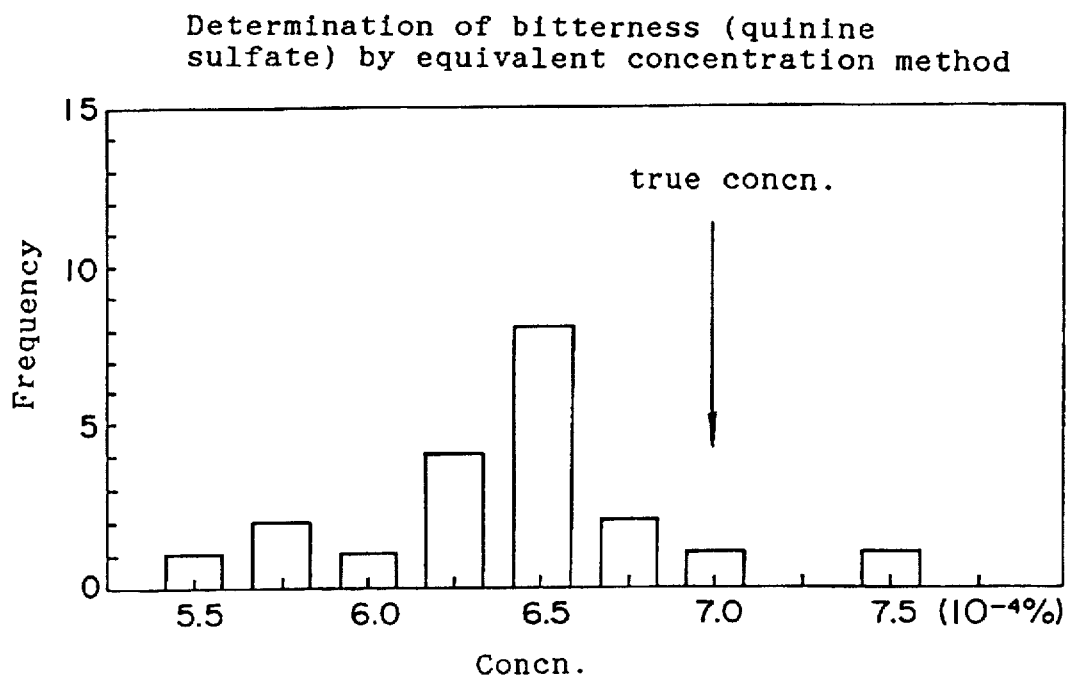
FIG. 3 is a bar graph showing the bitterness-depressing effect of one protein-lipid complex of the present invention.
Figure 4:
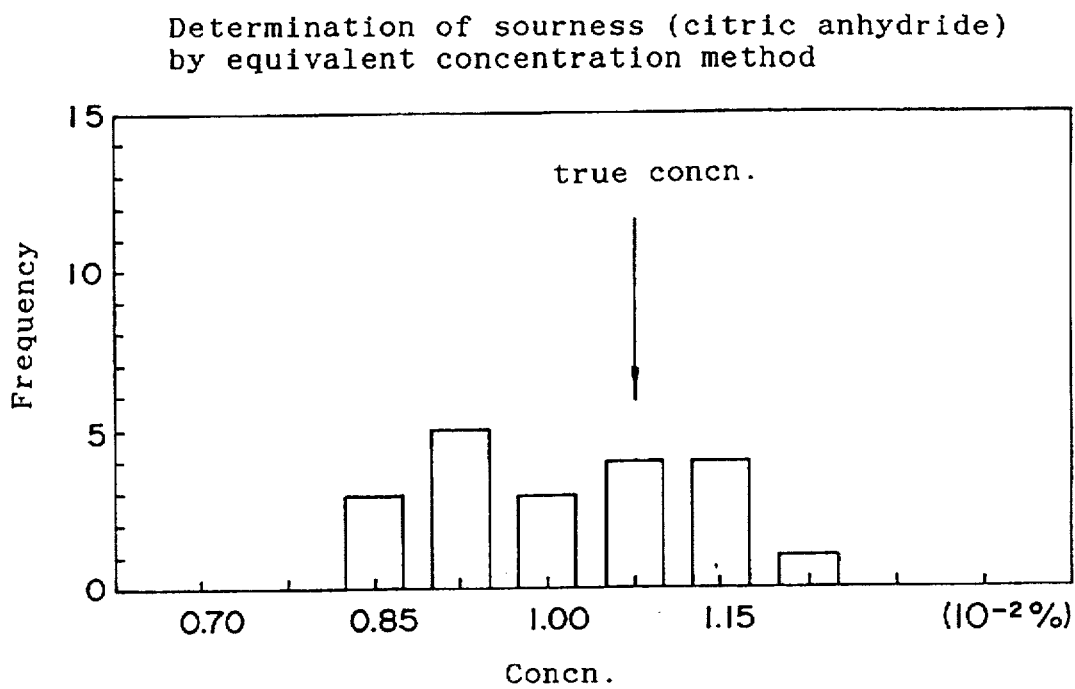
FIG. 4 is a bar graph showing the influence of one protein-lipid complex of the present invention upon sourness.
Figure 5:
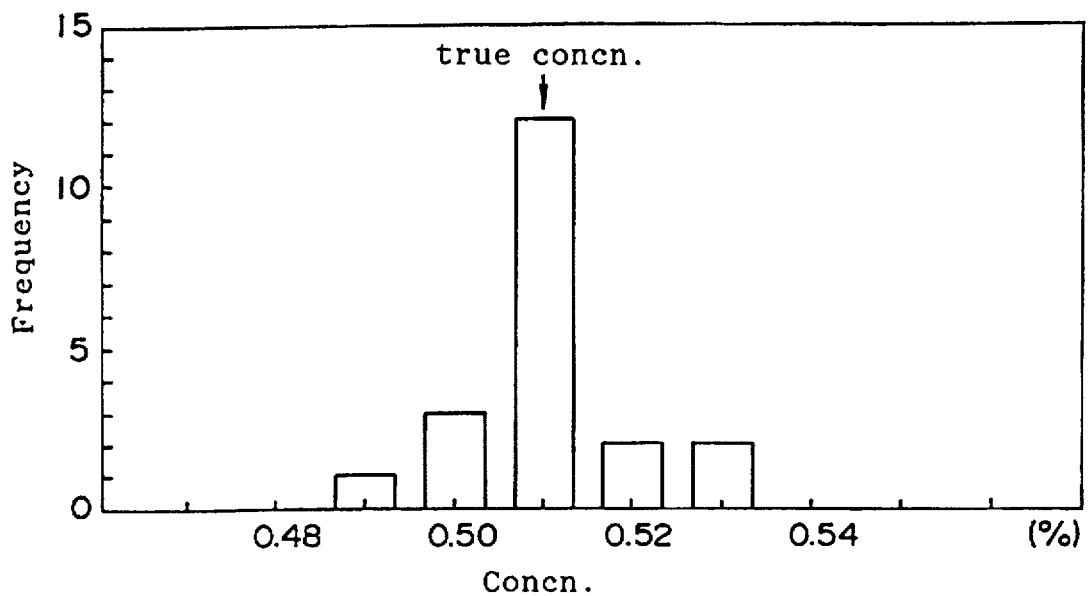
FIG. 5 is a bar graph showing the influence of one protein-lipid complex of the present invention upon saltiness.

Invention sample a was tested for its taste-modification effects upon five basic tastes by the equivalent concentration method. The "equivalent concentration method" refers to a method which comprises comparing the intensity of taste of a test solution with those of several standard solutions to determine which standard solution was equivalent to the test solution in the intensity of taste. Solutions each containing a tasting substance in a concentration specified in Table 1 were prepared and Invention sample "a" was added thereto in a final concentration of 0.1%. The results are given in FIGS. 1 to 5. As shown in FIGS. 1 and 2, the complex of the present invention exhibited an increasing effect upon sweetness and umami, while as shown in FIG. 3, it exhibited a depression effect upon bitterness. Further, as shown in FIGS. 4 and 5, the complex exerted little influence upon sourness and saltiness.

determining the stimulus threshold. Each examinee held the aqueous solutions of sucrose having various concentration at random and selected the solutions in which he or she sensed sweetness. The one having the minimum concentration among them which was selected by the examinee was regarded as the threshold. The results are given in Table 3. As is understood from the results in Table 3, lowered thresholds were observed with respect to the systems containing Invention sample "a", which reveals that the addition of the complex according to the present invention makes a person more sensitive to sweetness.

TABLE 3

| | Examinee | A | B | C | D | E | F | G | H | I | J | Average value |
|---|---|---|---|---|---|---|---|---|---|---|---|---|
| Sweetness threshold (%) | aq. sucrose soln. | 0.1 | 0.4 | 0.6 | 0.3 | 0.3 | 0.2 | 0.3 | 0.5 | 0.2 | 0.4 | 0.33 |
| | added 0.3% of Invention sample a | 0.1 | 0.1 | 0.2 | 0.3 | 0.2 | 0.1 | 0.1 | 0.2 | 0.1 | 0.1 | 0.15 |

TABLE 1

Test tasting substances and concentrations

| Kind of taste | Test tasting substance | Concn. of test soln. (%) |
|---|---|---|
| sweetness | sucrose | 1.0 |
| umami | sodium glutamate | 0.10 |
| bitterness | quinine sulfate | 0.00070 |
| sourness | citric anhydride | 0.01075 |
| saltiness | sodium chloride | 0.51 |

Example 2

Invention sample "b" was added to each test solution specified in the Table 1 in a final concentration of 0.3%. The obtained solutions were tested by the equivalent concentration method to examine the influences of the Invention sample "b" upon each taste. The results are given in Table 2. As is apparent from Table 2, the complex of the present invention increased sweetness and umami, depressed bitterness, and had no influence upon sourness and saltiness.

TABLE 2

| Kind of taste | Concn. recognized as to test soln. containing Invention sample b (%) | True concn. of test soln. (%) |
|---|---|---|
| sweetness | 1.15 | 1.0 |
| umami | 0.13 | 0.10 |
| bitterness | 0.00060 | 0.00070 |
| sourness | 0.0101 | 0.01075 |
| saltiness | 0.51 | 0.51 |

Example 3

Invention sample a was added to aqueous solutions of sucrose having various concentrations ranging from 0 to 0.6% in a final concentration of 0.3% and the effect of Invention sample "a" upon sweetness was evaluated by Example 4

Invention sample "b" was added to a commercially available milk containing 1.875% of sucrose in a final concentration of 0.1%. In a similar manner to that of Example 1, the equivalent concentration method was effected with the use of milk containing sucrose in various concentrations as the standard solution. As the result, the recognized sucrose concentration was 2.25%, which means that the complex of the present invention exhibited the effect in milk.

Example 5

Invention sample "c" was added to a 1.0% aqueous solution of sucrose and a 0.00070% aqueous solution of quinine sulfate each in a final concentration of 0.1%. The resulting solutions were tested by the equivalent concentration method. As the result, the recognized concentrations were 1.25% and 0.00058%, respectively.

Example 6

Figure 6:
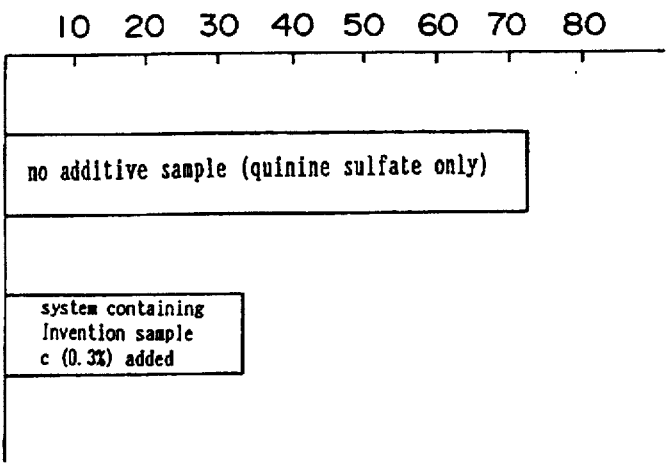
FIG. 6 is a bar graph showing the appearance of the influence of the protein-lipid complex of the present invention on the change in membrane potential caused by quinine sulfate.

Invention sample "c" was examined for taste-modifying effect by the use of a bitterness-responsive system using a model biomembrane. A single-lamellar liposome of azolectin was prepared according to the conventional process and the adsorption of quinine sulfate onto the liposome was determined. More precisely, the change in the intensity of fluorescence of a dyestuff sensitive to membrane potential, i.e., diS-$C_3$ (5) (a product of Japanese Research Institute for Photosensitizing Dyes Corporation) was determined by the method of Kumazawa et al. (Biochemistry, Vol. 27, p.1239, 1988) as an indication of the change in membrane potential due to the adsorption of quinine sulfate onto the membrane. The results are given in FIG. 6. It is presumed that the complex of the present invention acted on the membrane to depress bitterness.

Example 7

The capability of Invention sample "c" of adsorbing hydrophobic substances was determined by partitioning the Invnetion sample "c" in an organic solvent-water binary system (Yukagaku (Oil Chemistry), Vol. 30, No. 11, p.942). More precisely, the experimentation was effected as follows:

Invention sample "c" was added to 30 ml of a 0.02M pottasium phosphate buffer (pH:7.0) in a concentration of 3%. 10 ml of a 0.1% solution in n-heptane of n-octanol, n-decanol, n-dodecanol, δ-decalactone or δ-dodecalactone was superposed on the mixture thus obtained. The aqueous phase was mildly stirred with a magnetic stirrer and after 6 hours, the concentration of n-octanol, n-decanol, n-dodecanol, δ-decalactone or δ-dodecalactone in the n-heptane phase was determined by gas chromatography. A control sample, wherein no sample was added to the aqueous phase was prepared and the same procedure as described above was repeated to determine the concentrations. When the concentrations of n-octanol or the like in the n-heptane phase observed with respect to the control and those of n-octanol or the like in the n-heptane phase observed with respect to the system containing Invention sample "c" were abbreviated to "$C_n$" and "$C_s$", respectively, the amounts of n-octanol or the like partitioned to the aqueoues phases are represented by $W_n=\{1-(C_n/0.1)\}$ and $W_s=\{1-(C_s/0.1)\}$, respectively. Accordingly, the amount of n-octanol or the like adsorbed onto the Invention sample "c" is represented by the difference between the amounts thereof partitioned to the aqueous phases, i.e., $(W_s-W_n)\times 100$ (%). The results are given in Table 4.

TABLE 4

| Adsorbate | Adsorbed amount |
| --- | --- |
| n-octanol | 19.7 |
| n-decanol | 19.0 |
| n-dodecanol | 15.6 |
| δ-decalactone | 15.0 |
| δ-dodecalactone | 16.2 |

Example 8

Figure 7:
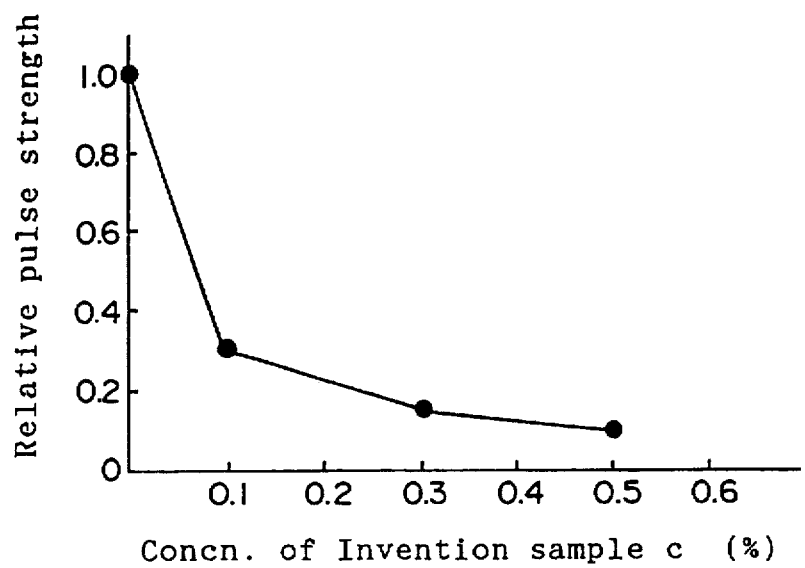
FIG. 7 is a graph showing the relationship between the amount of one protein-lipid complex of the present invention added and the response of the chorda tympani nerve system of a rat to stimulation when the complex is added to quinine sulfate.
Figure 8:
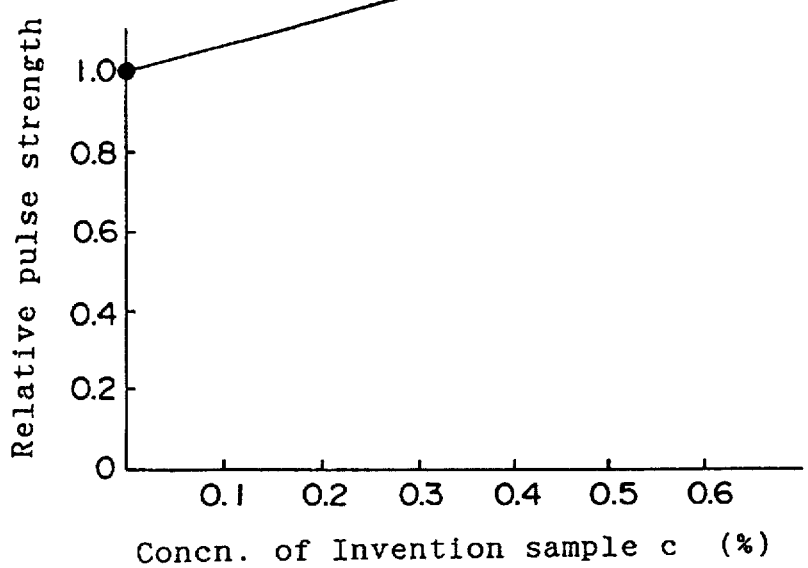
FIG. 8 is a graph showing the relationship between the amount of one protein-lipid complex of the present invention added and the response of the chorda tympani nerve system of a rat to stimulation when the complex is added to sucrose.

The gustatory responses of Invention sample "c" upon sweetness and bitterness were determined based on the response of the chorda tympani nerve system of a rat to stimulation. The lower jaw of a rat was cut to expose the funicular nerve. After a silver electric lump had been brought into contact with the funicular nerve, the electrical pulse generated by gustatory stimulation was conducted to an amplifier and recorded. 0.5 mM aqueous solutions of quinine sulfate or 1M aqueous solutions of sucrose containing Invention sample "c" in concentrations ranging from 0 to 0.5% were each circulated in the oral cavity of the rat to record the response potential. The results are given in FIGS. 7 and 8, respectively. It can be understood from the FIG. 7 that the stimulation by bitterness is decreased by the addition of the complex of the present invention, while it can be understood from the FIG. 8 that the stimulation by sweetness is increased thereby. Accordingly, it can be understood that the protein-lipid complex of the present invention acts at the taste receiving level.

Example 9

According to the following formulation, preparation process and evaluation method, a whipped cream and other whipped cream not containing Invention sample "d" were prepared and compared with each other in creamy flavor.

| Formulation | |
| --- | --- |
| (oil phase) | |
| hardened rapeseed oil (m.p.: 32.8° C.) | 20 pt. (by wt.) |
| hardened coconut oil (m.p.: 34.5° C.) | 6 |
| butter fat (m.p.: 32.4° C.) | 14 |
| lecithin | 0.28 |
| (aqueous phase) | |
| water | 54.5 |
| skimmilk powder | 4 |
| fatty acid ester of sucrose (HLB 11) | 0.2 |
| hexametaphosphoric acid | 0.1 |
| Invention sample "d" | 0.5 |

Preparation process

An oil phase and an aqueous phase were each prepared by dissolving or dispersing the raw materials in each other. According to the conventional process, a creamy fat-and-oil composition was prepared with the oil phase and the aqueous phase thus obtained through preliminary emulsification, high-pressure homogenization and sterilization. 80 g of granulated sugar was added to 1 l of the composition and the obtained mixture was whipped to give a whipped cream.

Evaluation

The whipped cream containing Invention sample "d" was organoleptically examined for creamy flavor by taking, as a control, a whipped cream not containing Invention sample "d". The results are given in Table 5. The figures in the Table 5 indicate each an average of the points graded by twenty expert panelists, in which a case wherein the control is superior to the sample is ranked as "−1"; a case wherein the control is slightly superior to the sample is ranked as "−0.5"; a case wherein the sample is equivalent to the control as "0"; a case wherein the sample is slightly superior to the control as "+0.5" and a case wherein the sample is superior to the control as "+1". As is apparent form Table 5, the product containing the complex of the present invention was such a cream that it exhibited a stronger milky flavor and a better body and was free from the disagreeable tastes such as bitterness and astringent taste, as compared with the product not containing the complex.

TABLE 5

| Evaluation item | whole | milkiness | body | sweetness | disagreeable taste |
| --- | --- | --- | --- | --- | --- |
| Point | 0.8 | 0.6 | 0.7 | 0.55 | −0.4 |

Example 10

The same procedure as that of Example 9 was repeated except that Invention sample "e" was used instead of Invention sample "d". The results are given in Table 6. By adding the complex of the present invention, the whipped cream was improved in flavor, as compared with the control.

TABLE 6

| Evaluation item | whole | milkiness | body | sweetness | disagreeable taste |
| --- | --- | --- | --- | --- | --- |
| Point | 0.6 | 0.5 | 0.5 | 0.4 | −0.4 |

Example 11

Invention samples "d" and "e" were each treated with SDS (sodium dodecyl sulfate) and mercaptan, and then were each subjected to SDS-polyacrylamide gel electrophoresis. The result of the electrophoresis was analyzed with a densitometer to determine the amounts of proteins. The results are given in Table 7. It is preferable for preparing a product excellent in flavor that the β-lactoglobulin content be 30% or above.

TABLE 7

| Protein | Sample | |
|---|---|---|
| | Invention sample d | Invention sample e |
| β-lactoglobulin | 80% | 32 |
| α-lactalbumin | 16% | 9 |
| α-casein | 0% | 43 |
| serum albumin | 2% | 5 |
| others | 2% | 11 |

Example 12

1 l of purified water was added to a mixture comprising 100 g of acetaminophen (acetamidophenol) and 60 g of Invention sample "d", followed by mixing. 150 g of synthetic aluminum silicate and mannitol were added to the mixture. The obtained mixture was further kneaded and vacuum-dried to give a powder. As compared with original acetaminophen powder, the obtained powder had little bitter taste.

Example 13

Each of the bitter-tasting cosmetic components listed in Table 8 and the protein-lipid complex prepared in the above Preparative Example 1 (Invention sample a) were dissolved or dispersed in water in predetermined concentrations (see Table 8), and the obtained solution or dispersion was evaluated for bitterness according to the following criteria. The results are given in Table 8.

| | |
|---|---|
| no bitter taste | 0 |
| slightly bitter taste | 1 |
| distinctly bitter taste | 2 |
| strongly bitter taste | 3 |
| severely bitter taste | 4 |
| severely bitter taste which remains even after rinse | 5 |

TABLE 8

| Cosmetic component | | | | | |
|---|---|---|---|---|---|
| | concn. | Concn. of protein-lipid complex | | | |
| Compd. | (wt %) | 0 wt % | 1.0 wt % | 3.0 wt % | 5.0 wt % |
| L-menthol | 0.10 | 3 | 2 | 2 | 1 |
| sodium mono-cetyl phosphate | 0.40 | 3 | 2 | 1 | 0 |
| sodium lauryl sulfate | 0.50 | 3 | 2 | 1 | 0 |
| linalol | 0.10 | 2 | 1 | 1 | 0 |
| phenylethyl alcohol | 0.10 | 2 | 1 | 0 | 0 |
| sucrose octaacetate | 0.01 | 5 | 4 | 3 | 2 |

Example 14

A dentifrice comprising the following components was prepared in the conventional manner:

| | |
|---|---|
| calcium secondary phosphate dihydrate | 45.0% |
| silicic acid anhydride | 2.0% |
| sorbitol | 15.0% |
| carboxymethylcellulose | 1.5% |
| sodium monolauryl phosphate | 2.0% |
| flavoring material | a proper amount |
| protein-lipid complex (Invention sample a) | 3.0% |
| water | the balance |

This dentifrice was one decreased in the bitterness due to sodium monolauryl phosphate.

Example 15

A mouthwash having the following composition was prepared in the conventional manner:

| | |
|---|---|
| ethanol | 15.0% |
| sorbitol | 10.0% |
| saccharin sodium | 0.15% |
| L-menthol | 0.10% |
| sodium lauryl sulfate | 0.10% |
| protein-lipid complex (Invention sample b) | 1.0% |
| water | the balance |

This mouthwash was one decreased in the bitterness due to L-menthol and sodium lauryl sulfate.

Example 16

A skin lotion having the following composition was prepared in the conventional manner:

| | |
|---|---|
| glycerol | 5.0% |
| 1,3-butanediol | 5.0% |
| denatured ethanol (containing 0.1% of sucrose octaacetate) | 10.0% |
| polyoxyethylene (20) octyl dodecyl ether | 1.0% |
| fragrance | a proper amount |
| protein-lipid complex (Invention sample c) | 0.5% |
| methyl paraben | 0.1% |
| water | the balance |

This skin lotion was one decreased in the bitterness due to sucrose octaacetate, so that the user was not displeased at the presence of the lotion remaining around the mouth after the application thereof.

Example 17

A milky lotion having the following composition was prepared in the conventional manner:

| | |
|---|---|
| cyclic silicone (pentamer) | 20.0% |
| squalane | 5.0% |
| polyoxyethylene-modified silicone | 5.0% |
| sodium lactate | 4.0% |
| methyl paraben | 0.1% |
| fragrance | a proper amount |
| protein-lipid complex (Invention sample d) | 2.0% |
| water | the balance |

This milky lotion was one decreased in the bitterness due to sodium lactate, so that the user was not displeased at the bitterness even when the milky lotion was applied to the circumference of the mouth.

Example 18

A face cleansing preparation having the following composition was prepared:

| | |
|---|---|
| triethanolamine monolauryl phosphate | 20.0% |
| laurylbetaine | 5.0% |
| glycerol | 5.0% |
| polyoxyethylene (100) oleyl ether | 2.0% |
| protein-lipid complex (Invention sample e) | 5.0% |
| water | the balance |

This face cleansing preparation exhibited little bitterness even when it accidentally enters the mouth in washing the face.

Example 19

A mouth freshener having the following composition was prepared:

| | |
|---|---|
| ethanol | 35.0% |
| glycerol | 10.0% |
| polyoxyethylene hardened castor oil | 1.0% |
| L-menthol | 0.5% |
| chlorohexidine gluconate | 0.02% |
| protein-lipid complex (Invention sample f) | 1.0% |
| water | the balance |

This mouth freshener had little bitter taste in spite of its high L-menthol content, and exhibited a high refreshing effect.

Example 20

10 g of a whey protein comprising β-lactoglobulin, lactalbumin and casein was kneaded with 8 g of soybean lecithin (trade name: SLP White, a product of True Lecithin Mfg. Co., Ltd.). The obtained kneaded mixture was dispersed in 50 ml of water and the obtained dispersion was homogenized with a homogenizer. The obtained emulsion was dehydrated under the conditions of 45° C. and 0.1 Torr one whole day and night to give 15 g of a whey protein-lecithin complex having a water content of 8.5% by weight (Invention sample 1).

This complex was evaluated for the decreasing effect on the bitterness of pharmaceuticals.

The bitterness-decreasing effect can quantitatively be evaluated by determining the response of the glossopharyngeal nerve of a frog to the stimulation of the lingual surface thereof. The response of the gustatory organ of a frog to bitterness has a characteristic in that the bitterness threshold highly correlates with the results of human organoleptic test. Accordingly, the response of the gustatory organ of a frog to bitterness is usable as a system for the quantitative evaluation of the bitterness-decreasing effect.

The outside of the lower jaw of a frog was cut under urethane anesthesia to expose the glossopharyngeal nerve. The glossopharyngeal nerve was cut on its center side and brought into contact with a silver-silver chloride electrode on its periphery side. The electrical pulse (nerve impulse) caused by the stimulation by bitterness was amplified and integrated and thereafter recorded on a pen recorder. The height of the response observed just after the stimulation was taken as the response intensity to bitterness. The stimulation of the lingual surface was conducted by using the test liquids which will be described below each in a total amount of 10 ml at a flow rate of 1.5 ml/sec.

The complex of the present invention was examined for bitterness-decreasing effects on quinine hydrochloride, strychnine nitrate and papaverine as bitter-testing pharmaceuticals.

Test liquids (1) 0.1 mM aqueous solution of quinine hydrochloride.

(2) a liquid prepared by adding the Invention sample 1 to a 0.1 mM aqueous solution of quinine hydrochloride in a final concentration of 0.5% by weight, stirring and mixing.

(3) 1 mM aqueous solution of strychnine nitrate.

(4) a liquid prepared by adding the Invention sample 1 to a 1 mM aqueous solution of strychnine nitrate in a final concentration of 0.5% by weight, stirring and mixing.

(5) 10 mM aqueous solution of papaverine.

(6) a liquid prepared by adding the Invention sample 1 to a 10 mM aqueous solution of papaverine in a final concentration of 0.5% by weight, stirring and mixing.

Figure 9:
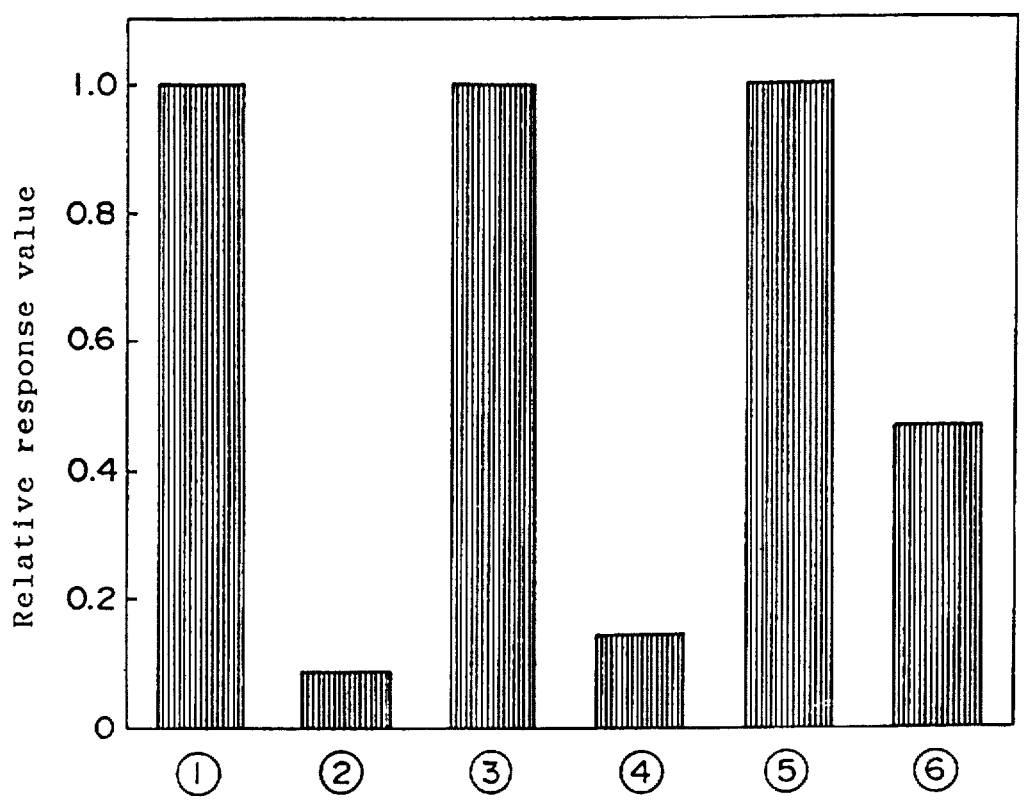
FIG. 9 is a bar graph showing the depression effects of one protein-lipid complex of the present invention upon the bitternesses of quinine, strychnine and papaverine.

The results are given in FIG. 9.

(2), (4) and (6) are Examples, and (1), (3) and (5) are controls corresponding thereto, respectively.

As shown in the FIG. 9, the responses to the bitterness of these bitter-tasting pharmaceuticals were all decreased by the addition of the complex of the present invention.

Example 21

10 g of β-lactoglobulin was kneaded with 8 g of phosphatidic acid and the obtained kneaded mixture was dispersed in 50 ml of water. The obtained dispersion was homogenized with a homogenizer. The obtained emulsion was dehydrated under the conditions of 45° C. and 0.1 Torr one whole day and night to give 15 g of a β-lactoglobulin-phosphatidic acid complex having a water content of 11.2% by weight (Invention sample 2).

The Invention sample 2 was evaluated for the bitterness-decreasing effects on caffeine and L-leucine as bitter-tasting substances in pharmaceuticals by determining the response of the glossopharyngeal nerve of a frog.

After a 0.3% dispersion of the Invention sample 2 was preliminarily held in the mouth of a frog for 10 minutes, an aqueous solution of caffeine or leucine was brought into contact with the lingual surface to simulate the tongue. After water was held in the mouth of a frog for 10 minutes as a control, the tongue was stimulted with an aqueous solution of caffeine or leucine to determine the response of the glossopharyngeal nerve of a frog.

Determination (1) response to the stimulation by a 40 mM aqueous solution of caffeine after holding water for 10 minutes.

(2) response to the stimulation by a 40 mM aqueous solution of caffeine after holding a 0.3% dispersion of Invention sample 2 for 10 minutes.

(3) response to the stimulation by a 100 mM aqueous solution of L-leucine after holding water for 10 minutes.

(4) response to the stimulation by a 100 mM aqueous solution of L-leucine after holding a 0.3% aqueous dispersion of Invention sample 2 for 10 minutes.

Figure 10:
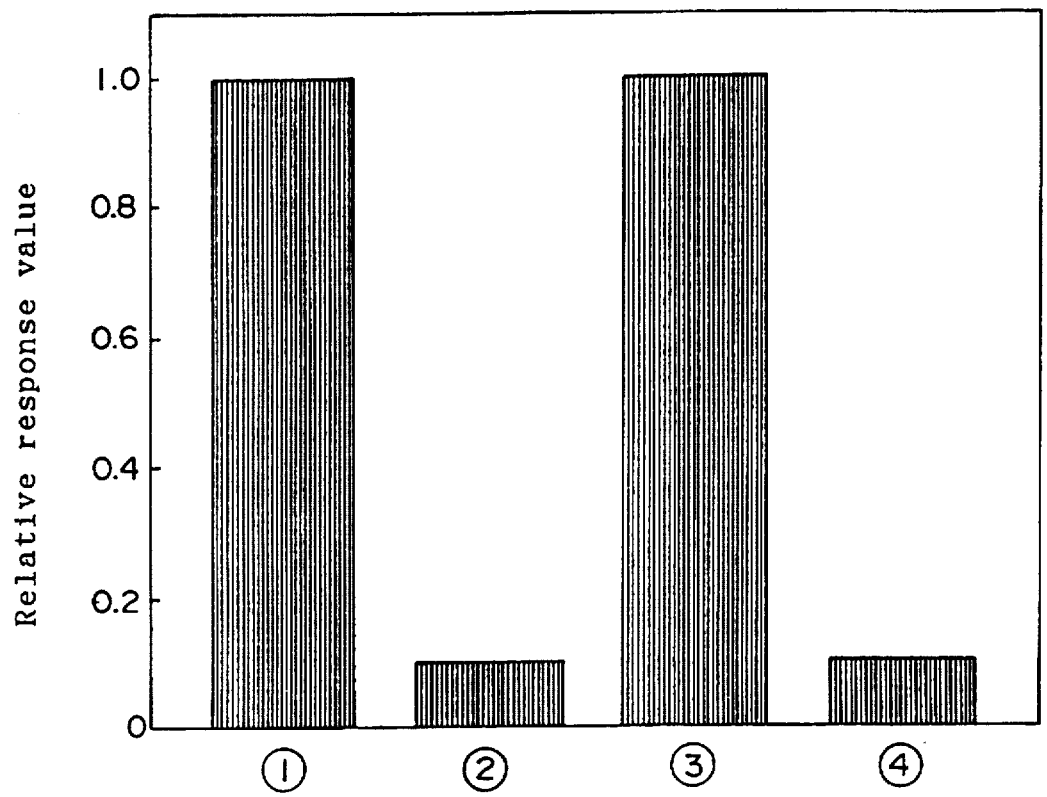
FIG. 10 is a bar graph showing the depression effects of one protein-lipid complex of the present invention upon the bitternesses of caffeine and L-leucine.

The results are given in FIG. 10.

As is apparent from FIG. 10, every response to bitterness was decreased by pretreating the mouth of the frog with a 0.3% dispersion of the Invention sample 2.

Example 22

Invention sample 2 was added to a 1 mM aqueous solution of strychnine nitrate in a final concentration of 0.5% by weight. The obtained mixture was stirred to give a suspension. This suspension and a 1 mM aqueous solution of strychnine nitrate as a control were organoleptically evaluated for bitterness by twenty panelists for gustatory evaluation according to the following criteria:

| | |
|---|---|
| very strongly bitter | 5 |
| strongly bitter | 4 |
| bitter | 3 |
| slightly bitter | 2 |
| not bitter | 1 |

The results are given in Table 9. In Table 9, the average values of the grades obtained by the above organoleptic evaluation are shown. As is apparent from Table 9, the bitterness of strychnine nitrate was decreased by the addition of Invention sample 2.

TABLE 9

| Test sample | Organoleptic evaluation of bitterness (average value) |
|---|---|
| 1 mM aqueous solution of strychnine nitrate | 4.8 |
| added 0.5% by weight of Invention sample 2 to the above aqueous solution | 1.4 |

Example 23

0.1 g of crude caffeine powder was dissolved in 50 ml of deionized water, followed by the addition of 10 g of β-lactoglobulin and 8 g of phosphatidylcholine and stirring. The obtained mixture was homogenized with a homogenizer. The obtained emulsion was dehydrated by the use of a freeze dryer to give 16 g of a caffeine powder containing the bitterness-masking agent of the present invention, i.e., the protein-lipid complex. This caffeine powder tasted little bitter.

Example 24

100 g of ovalbumin originating in egg white was kneaded with 40 g of a lecithin prepared by enzymolysis and containing phosphatidylinositol and phosphatidic acid. 1000 ml of water was added to the obtained kneaded mixture. The obtained mixture was emulsified with a homomixer until being homogeneous. The obtained emulsion was dehydrated under the condition of 0.1 Torr one whole day and night to give 125 g of an ovalbumin-lecithin (prepared by enzymolysis) complex (Invention sample 3).

Invention sample 3 was added to grapefruit juice in final concentrations of 0.1 and 0.3% (weight ratio) to determine whether Invention sample 3 has the bitterness-decreasing effect to the grapefruit juice or not.

The grapefruit juices containing Invention sample 3 and one not containing it were examined for the intensity of the bitterness according to the five criteria as will be described below. Ten persons of both sexes aged from 20 to 46 and having a normal sensitivity for taste were selected as panelists.

| Intensity of bitterness | 5 | strongly bitter |
|---|---|---|
| | 4 | bitter |
| | 3 | somewhat bitter |
| | 2 | sensibly bitter |
| | 1 | not bitter |

The results are given in Table 10. The figures in Table 10 are the average values of the grades evaluated.

TABLE 10

| Test sample | Concn. of Invention sample 3 added | Average value of intensity of bitterness |
|---|---|---|
| (1) grapefruit juice | — | 4.2 |
| (2) one obtained by adding Invention sample 3 to (1) | 0.1% | 1.4 |
| (3) one obtained by adding Invention sample 3 to (1) | 0.3% | 1.0 |

Example 25

10 g of whey protein was kneaded with 4 g of an acidic phospholipid mixture comprising phosphatidylinositol, phosphatidylserine, phosphatidylglycerol and phosphatidic acid, and 100 ml of water was added to the obtained kneaded mixture. The obtained mixture was dispersed and homogenized by treating with a homogenizer. The obtained emulsion was dehydrated under the condition of 0.1 Torr one whole day and night to give 14 g of a whey protein-acidic phospholipid complex (Invention sample 4). Invnetion sample 4 was added to coffee to determine whether Invention sample 4 exhibits the decreasing effect of the bitterness of coffee or not. Invention sample 4 was added to coffee in final concentrations of 0.1 and 0.3%. The intensity of the bitterness was evaluated according to the same five criteria as those of the Example 24. The results are given in Table 11.

TABLE 11

| Test sample | Concn. of Invention sample 4 added | Average value of intensity of bitterness |
|---|---|---|
| (1) coffee | — | 4.1 |
| (2) one obtained by adding Invention sample 4 to (1) | 0.1% | 2.4 |
| (3) one obtained by adding Invention sample 4 to (1) | 0.3% | 1.6 |

Example 26

100 g of a whey protein comprising β-lactoglobulin, α-lactalbumin and casein was kneaded with 40 g of soybean lecithin and the obtained kneaded mixture was dispersed in 1000 ml of water. The obtained dispersion was homogenized with a homogenizer. The obtained emulsion was freeze-dried under the conditions of 20° C. and 0.1 Torr one whole day and night to give 130 g of a whey protein-soybean lecithin complex having a water content of 8.5% by weight (Invention sample 5).

A whipped cream was prepared according to the same formulation and preparation process as those of Example 9 except that Invention sample 5 was used instead of Invention sample "d", and the whipped cream containing Invnention sample 5 was examined for creamy flavor in the same manner as that of Example 9.

The results are given in Table 12. As shown in Table 12, the product containing Invention sample 5 was such a cream that it exhibited a stronger milky flavor and a better body and was free from the disagreeable tastes such as bitterness and astringent taste, as compared with the product not containing Invention sample 5.

TABLE 12

| Evaluation item | whole | milkiness | body | sweetness | disagreeable taste |
|---|---|---|---|---|---|
| Point | 0.8 | 0.6 | 0.7 | 0.55 | −0.4 |

Example 27

10 g of soybean protein was mixed with 5 g of phosphatidic acid, and 100 ml of water was added to the resulting mixture. The obtained mixture was dispersed and homogenized with a homogenizer. The obtained emulsion was spray-dried to give 14 g of a soybean protein-phosphatidic acid complex (Invention sample 6).

By adding Invention sample 6 to a powdered soup, the soup became free from disagreeable tastes, increased in body and improved in savor, and an excellent product was obtained.

Example 28

10 g of β-lactoglobulin was mixed with 4 g of phosphatidic acid, and 100 ml of water was added to the resulting mixture. The obtained mixture was dispersed and homogenized with a homogenizer. The obtained emulsion was freeze-dried to give 13 g of a β-lactoglobulin-phosphatidic acid complex (Invention sample 7).

Invention sample 7 was added to an aqueous solution (5 mM) of promethazine hydrochloride used as the raw material of pharmaceuticals to evaluate whether Invention sample 7 exhibits a bitterness-decreasing effect on it or not. More precisely, the intensity of the bitterness was evaluated according to the equivalent concentration method (see Example 1). For comparison, those containing, instead of Invention sample 7, sucrose, sorbitol and β-lactoglobulin, respectively which were used for the purpose of decreasing the bitterness in liquid preparations, were also evaluated in a similar manner to that described above. The results are given in Table 13.

As shown in Table 13, a solution of promazine hydrochloride having a decreased bitterness could be obtained by adding Invention sample 7.

TABLE 13

| Test substance | Concn. of test substance | Intensity of bitterness |
|---|---|---|
| (1) — (control) | — | 9.2 |
| (2) Invention sample 7 | 0.3% | 5.0 |
| (3) Invention sample 7 | 3% | 2.8 |
| (4) sucrose | 20% | 7.1 |
| (5) sorbitol | 30% | 6.9 |
| (6) β-lactoglobulin | 3% | 9.0 |

Further, liquid preparations containing Invention sample 7 and one of pharmaceuticals A to G which will be described below were prepared in the same manner as that described above except that pharmaceuticals A to G were each used instead of the promethazine hydrochloride. The obtained liquid preparations were examined for taste. They were freed from the disagreeable bitterness inherent in pharmaceuticals and were easy to take orally.

A quinine
B chlorpromazine
C papaverine
D propranolol
E berberine
F brucine
G strychnine

Example 29

10 of egg white albumin containing ovalbumin was kneaded with 4 g of phosphatidic acid and 2 g of phosphatidylinositol, and 100 ml of water was added to the obtained kneaded mixture. The obtained mixture was dispersed and homogenized by treating with a homogenizer. The obtained emulsion was dehydrated under the conditions of 20° C. and 0.1 Torr one whole day and night to give 15 g of an albumin-phosphatidic acid-phosphatidylinositol complex (Invention sample 8).

1 g of acetaminophen was mixed with 20 g of Invention sample 8, and 100 ml of purified water was added to the obtained mixture, followed by agitation. Further, 5 g of synthetic aluminum silicate and mannitol were added thereto, and the obtained mixture was blended and vacuum-dried to give a powder. The bitterness of the powder thus obtained was compared with that of crude acetaminophen powder. This powder tasted little bitter.

Example 30

10 g of Invention sample 7 obtained in Example 28 was mixed with 0.5 g of promazine in a mortar to give a powder. This powder tasted less bitter than crude promazine powder.

Example 31

Invention sample 7 obtained in Example 28 was added to deionized water in a final concentration of 3.0%. Then, the obtained mixture was stirred to disperse Invention sample 7. The dispersion of β-lactoglobulin-phosphatidic acid complex thus obtained (Invention sample 9) was held in the mouth for about 10 seconds and then rinsed the oral cavity to fully spread the dispersion in the oral cavity. Thereafter, Invention sample 9 was spit out and a pharmaceutical having a bitter taste was held in the mouth to evaluate the bitter taste. For comparison, the intensity of the bitterness of the pharmaceutical was evaluated in the same manner as described above was repeated except that water or a 10% aqueous solution of sucrose was used instead of Invention sample 9. The evaluation of the intensity of the bitterness was conducted by ten healthy persons of both sexes in their twenties to forties according to the criteria which will be described below.

Subjects of evaluation (1) Intensity of the bitterness of caffeine sensed when a 50 mM aqueous solution of caffeine is held in the mouth after 10-second hold of Invention sample 9 in the mouth and rinse of the mouth therewith.

(2) Intensity of the bitterness of caffeine sensed when a 50 mM aqueous solution of caffeine is held in the mouth after 10-second hold of water in the mouth and rinse of the mouth therewith.

(3) Intensity of the bitterness of caffeine sensed when a 50 mM aqueous solution of caffeine is held in the mouth after 10-second hold of a 10% aqueous solution of sucrose in the mouth and rinse of the mouth therewith.

(4) Intensity of the bitterness of quinine sensed when a 0.5 mM aqueous solution of quinine is held in the mouth after 10-second hold of Invention sample 9 in the mouth and rinse of the mouth therewith.

(5) Intensity of the bitterness of quinine sensed when a 0.5 mM aqueous solution of quinine is held in the mouth after 10-second hold of water in the mouth and rinse of the mouth therewith.

(6) Intensity of the bitterness of quinine sensed when a 0.5 mM aqueous solution of quinine is held in the mouth after 10-second hold of a 10% aqueous solution of sucrose in the mouth and rinse of the mouth therewith.

| Criteria for evaluation |
|---|
| 0 to 2 . . . not bitter |
| 3 to 4 . . . slightly bitter |
| 5 to 6 . . . somewhat bitter |
| 7 to 8 . . . strongly bitter |
| 9 to 10 . . . very strongly bitter |

Figure 11:
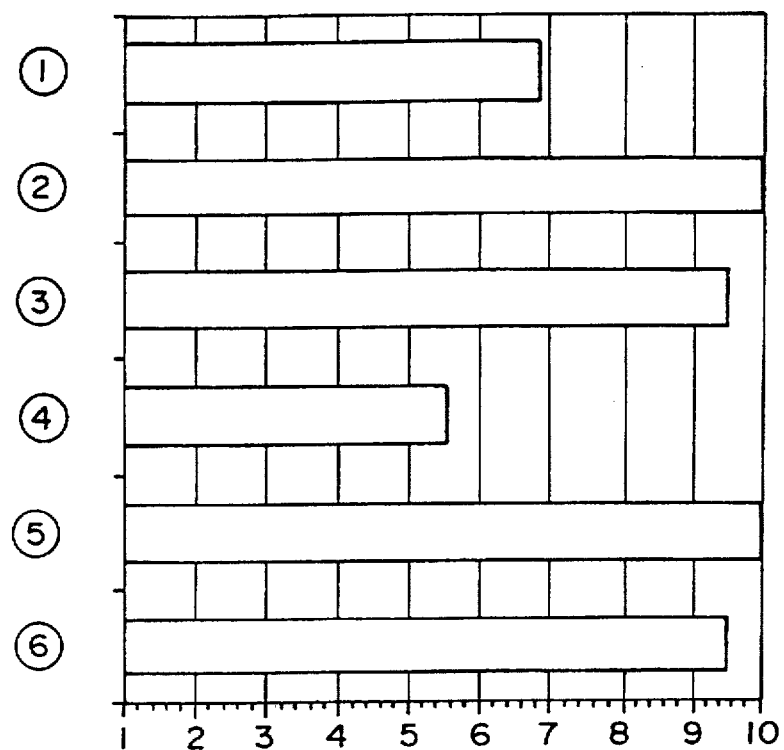
FIG. 11 is a bar graph showing the depression effects of one protein-lipid complex of the present invention upon the bitternesses of caffeine and quinine.

The results are given in FIG. 11. In FIG. 11, the average values of the intensities of the bitterness are shown.

As is apparent from FIG. 11, Invention sample 9 which comprises an aqueous dispersion of Invention sample 7 exhibited a stronger bitterness-decreasing effect than that of an aqueous solution of sucrose which has hitherto been used as a bitterness-decreasing agent for pharmaceuticals.

Example 32

100 g of ovalbumin and 40 g of phosphatidic acid were dispersed in 1000 ml of water and then the obtained dispersion was homogenized with a homogenizer. The obtained emulsion was dehydrated under the conditions of 20° C. and 0.1 Torr one whole day and night to give 130 g of an ovalbumin-phosphatidic acid complex (Invention simple 10). 50 g of Invention sample 10, 40 g of mannitol and 40 g of synthetic aluminum silicate were weighed and added to 500 ml of water. The obtained mixture was stirred and spray-dried to give 90 g of Invention sample 11 in the form of powder.

3 g of Invention sample 11 was held in the mouth and bitten for about 15 seconds. Thereafter, a 5 mM aqueous solution of promazine was held in the mouth. A less bitter taste was recognized as compared with the case wherein a 5 mM aqueous solution of promazine was held in the mouth without holding Invention sample 11 in the mouth.

We claim:

1. A method of decreasing the bitterness of a pharmaceutical which comprises mixing an effective bitterness-decreasing amount of a protein phospholipid complex with a bitter tasting pharmaceutical component wherein said protein is selected from the group consisting of milk protein, soybean protein and egg protein.

2. The method of reducing bitterness according to claim 1, wherein a liquid composition containing said protein phospholipid complex in an amount from 0.1 to 20% by weight of the total liquid weight is mixed with the bitter-tasting pharmaceutical component.

3. The method of reducing bitterness according to claim 1, wherein a paste or solid containing said protein phospholipid complex in an amount from 10 to 500 parts by weight based on 1 part of the paste or solid is mixed with the bitter-tasting pharmaceutical component.

4. The method according to claim 1, wherein said phospholipid is a negatively charged acidic phospholipid.

5. The method according to claim 1, wherein said complex is a whey protein/soybean lecithin complex.

6. The method according to claim 1, wherein said complex is a beta-lactoglobulin/phosphatidic acid complex.

7. The method according to claim 1, wherein said complex is an ovalbumin-phosphatidic acid-phosphatidylinositol complex.

8. A method for decreasing the bitterness of a food which comprises mixing an effective bitterness decreasing amount of a complex of ovalbumin and enzymatically prepared lecithin with a bitter tasting food component.

9. A method for decreasing the bitterness of a food which comprises mixing an effective bitterness decreasing amount of a whey protein/acidic phospholipid complex with a bitter tasting food component.

10. A method for decreasing the bitterness of a food which comprises mixing an effective bitterness decreasing amount of a soybean protein/phosphatidic acid complex with a bitter tasting food component.

11. The method of decreasing bitterness according to claim 8, wherein said protein phospholipid complex is present in an amount from 0.5 to 10% by weight as compared to the food component.

12. The method of decreasing bitterness according to claim 9, wherein said protein phospholipid complex is present in an amount from 0.05 to 10% by weight as compared to the food component.

13. The method of decreasing bitterness according to claim 10, wherein said protein phospholipid complex is present in an amount from 0.05 to 10% by weight as compared to the food component.

14. The method of decreasing bitterness according to claim 11, wherein said protein-lipid complex is present in an amount from 0.1 to 3% by weight of the food component.

15. The method of decreasing bitterness according to claim 12, wherein said protein-lipid complex is present in an amount from 0.1 to 3% by weight of the food component.

16. The method of decreasing bitterness according to claim 13, wherein said protein-lipid complex is present in an amount from 0.1 to 3% by weight of the food component.

17. The method of decreasing bitterness according to claim 1, wherein the pharmaceutical component is selected from the group consisting of promazine, quinine, chlorpromazine, papaverine, propranolol, berberine, brucine and strychnine.

* * * * *